United States Patent
Huang et al.

(10) Patent No.: US 9,360,544 B2
(45) Date of Patent: Jun. 7, 2016

(54) ACCELERATED MR THERMOMETRY MAPPING INVOLVING AN IMAGE RATIO CONSTRAINED RECONSTRUCTION

(75) Inventors: Feng Huang, Gainesville, FL (US); Max Oskar Köhler, Espoo (FI); Jukka Iimari Tanttu, Espoo (FI); Wei Lin, Gainesville, FL (US)

(73) Assignee: Koninklijke Philips N.V., Eindhoven (NL)

( * ) Notice: Subject to any disclaimer, the term of this patent is extended or adjusted under 35 U.S.C. 154(b) by 359 days.

(21) Appl. No.: 14/001,941

(22) PCT Filed: Feb. 3, 2012

(86) PCT No.: PCT/IB2012/050504
§ 371 (c)(1),
(2), (4) Date: Aug. 28, 2013

(87) PCT Pub. No.: WO2012/117303
PCT Pub. Date: Sep. 7, 2012

(65) Prior Publication Data
US 2013/0338484 A1 Dec. 19, 2013

Related U.S. Application Data

(60) Provisional application No. 61/447,732, filed on Mar. 1, 2011.

(51) Int. Cl.
*A61B 5/055* (2006.01)
*G01R 33/56* (2006.01)
(Continued)

(52) U.S. Cl.
CPC ............... *G01R 33/56* (2013.01); *A61B 18/02* (2013.01); *A61N 5/00* (2013.01); *A61N 5/0625* (2013.01);
(Continued)

(58) Field of Classification Search
CPC ....... A61B 18/02; A61N 5/00; A61N 5/0625; A61N 7/02; G01R 33/4804; G01R 33/4814; G01R 33/56; G01R 33/561; G01R 33/5611
See application file for complete search history.

(56) References Cited

U.S. PATENT DOCUMENTS

2005/0020897 A1 1/2005 Fuderer
2008/0292167 A1 11/2008 Todd
(Continued)

FOREIGN PATENT DOCUMENTS

| JP | 0884740 A | 4/1996 |
| JP | 2000300591 A | 10/2000 |
| JP | 2003325510 A | 11/2003 |
| WO | 2008137783 A2 | 11/2008 |

OTHER PUBLICATIONS

Huang, Yumei et al "A Fast Total Variation Minimization Method for Image Restoration", Multiscale Model Somul. 2008 Society for Inductrial and Applied Mathematics, vol. 7, No. 2, pp. 774-795.
Doneva, Mariya et al "Compressed Sensing Reconstruction for Magnetic Resonance Parameter Mapping", Magnetic Resonance in Medicine, vol. 64, 2010, pp. 114-1120.
Gamper, Urs et al "Compressed Sensing in Dynamic MRI", Magnetic Resonance in Medicine, vol. 59, 2008, pp. 365-373.
Griswold, Mark A. et al Generalized Autocalibrating Partially Parallel Acquisitions (GRAPPA), Magnetic Resonance in Medicine vol. 47, 2002, pp. 1202-1210.
(Continued)

*Primary Examiner* — Ruth S Smith

(57) ABSTRACT

A medical apparatus (300, 400, 500, 600) includes a magnetic resonance imaging system (301). The medical apparatus further includes a memory (330) containing instructions (350, 352, 354, 456, 458, 460) for execution by a processor (324). Execution of the instructions causes the processor to acquire (102, 202) baseline magnetic resonance data (332) and reconstruct (104, 204) a first image (334) using the baseline magnetic resonance data. Execution of the instructions further causes the processor acquire (106, 212) undersampled magnetic resonance data (336), which is undersampled in k- space in comparison to the baseline magnetic resonance data. Execution of the instructions further causes the processor reconstruct (108, 214) a second image (338) using the undersampled magnetic resonance data and the first image. The second image is reconstructed using an image ratio constrained reconstruction algorithm (354). A temperature map (340) is calculated (110, 216) using the second image.

18 Claims, 7 Drawing Sheets

(51) Int. Cl.
| | |
|---|---|
| G01R 33/48 | (2006.01) |
| A61B 18/02 | (2006.01) |
| A61N 5/00 | (2006.01) |
| A61N 5/06 | (2006.01) |
| A61N 7/02 | (2006.01) |
| G01R 33/561 | (2006.01) |

(52) U.S. Cl.
CPC .............. *A61N 7/02* (2013.01); *G01R 33/4804* (2013.01); *G01R 33/4814* (2013.01); *G01R 33/561* (2013.01); *G01R 33/5611* (2013.01)

(56) References Cited

U.S. PATENT DOCUMENTS

| | | | | |
|---|---|---|---|---|
| 2008/0298661 | A1* | 12/2008 | Huang | G01R 33/5611 382/131 |
| 2014/0091793 | A1* | 4/2014 | Guo | G01R 33/56341 324/309 |
| 2015/0190659 | A1* | 7/2015 | Kohler | A61N 7/02 600/411 |

OTHER PUBLICATIONS

Guo, W et al "Combine Reconstructions using Non-Local Operator and its Application in PPI", Proc. Intl. Soc. Mag. Reson. Med. vol. 17, 2009, p. 4642.

Lustig, Michael et al "Sparse MRI: The Application of Compressed sensing for Rapid MR Imaging", Magnetic Resonance in Medicine, vol. 58, 2007, pp. 1182-1195.

Chen, Yunmei et al "A Novel Method and Fast Algorithm for MR Image Reconstruction with Significantly under-Sampled Data", Inverse Problems and Imaging, vol. 4, No. 2, 2010, pp. 223-240.

Pruessmann, Klaas P. et al "SENSE: Sensitivity Encoding for Fast MRI", Magnetic Resonance in Medicine, vol. 42, 1999, pp. 952-962.

Lustig, Michael El Al "SPIRIT: Iterative Self-Consistent Parallel Imaging Reconstruction from Arbitrary k-Space", Magnetic Resonance in Medicine, vol. 64, 2010, pp. 457-471.

Huang, Feng et al "Partial Fourier Reconstruction through Data Fitting and Convolution in k-Space", Magnetic Resonance in Medicine, vol. 62, 2009, pp. 1-9.

Beck, Amir et al "A Fast Iterative Shrinkage-Thresholding Algorithm for Linear Inverse Problems", Siam J. Imaging Sciences vol. 2, No. 1, 2009, pp. 183-202.

Huang, Feng "Image Ratio Constrained Reconstruction" (IRCR) 2007, Sedona, Arizona, p. 51.

Lai, R. et al "Efficient L1SPIRiT Reconstruction (ESPIRiT) for Highly Accelerated 3D Volumetric MRI with Parallel Imaging and Compressed Sensing", 2010, Stockholm, Sweden, p. 345.

Trzaslo, J.D. et al "Nonconvex Compressive Sensing with Parallel Imaging for Highly Accelerated 4D CD-MRA", 2010, Stockholm, Sweden pp. 347.

Wlodarczyk, et al "Three-Dimensional Monitoring of Small Temperature Changes for Therapeutic Hyperthermia using MRI", Journal of Magnetic Resonance Imaging, vol. 8, 1998, pp. 165-174.

* cited by examiner

ACCELERATED MR THERMOMETRY MAPPING INVOLVING AN IMAGE RATIO CONSTRAINED RECONSTRUCTION

CROSS-REFERENCE TO PRIOR APPLICATIONS

This application is the U.S. National Phase application under 35 U.S.C. §371 of International Application No. PCT/IB2012/050504, filed on Feb. 3, 2012, which claims the benefit of U.S. Provisional Patent Application No. 61/447,732, filed on Mar. 1, 2011. These application are hereby incorporated by reference herein.

TECHNICAL FIELD

The invention relates to magnetic resonance thermometry, in particular a means of accelerating thermal mapping by reconstructing undersampled magnetic resonance data with previously acquired magnetic resonance data.

BACKGROUND OF THE INVENTION

In recent years magnetic resonance thermometry has been coupled with various means of heating or cooling tissue for therapy. Measuring the effect of the tissue heating or cooling allows the guiding of the therapy and also the ability to assess the effect of a therapeutic treatment on a subject.

In high-intensity focused ultrasound (HIFU) therapy, reliable real-time temperature monitoring using e.g. MRI is necessary to ensure a sufficient thermal necrosis to the target while avoiding excessive heating and damage of surrounding healthy tissues. To achieve sufficient temporal and spatial resolution, fast imaging is required preferably with a high spatial resolution while maintaining a sufficient SNR for reconstruction of reliable temperature measurements.

In Wlodarczyk et. al., "Three-Dimensional Monitoring of Small Temperature Changes for Therapeutic Hyperthermia Using MRI," Journal of Magnetic Resonance Imaging, Vol. 8, pp. 165-174, the keyhole technique was used to accelerate magnetic resonance temperature using a pulsed diffusion gradient spin echo pulse sequence.

SUMMARY OF THE INVENTION

MRI (Magnetic Resonance Imaging) is often used to plan and guide HIFU as well as other thermal therapies. MR (Magnetic Resonance) has the benefit over other imaging modalities in that it is able to produce high-quality temperature images since several parameters are temperature dependent. The most commonly adopted approach is to use the proton resonance frequency (PRF) shift of water, which is linearly dependent on temperature. Other alternative methods of thermometry rely on the temperature dependence of the T1, T2 or T2-star relaxation times or the proton density. However, the temperature dependence is small, and tissue-dependent, which are the main reasons why PRF thermometry is the by far most used method. Though the other thermometry techniques rely on the magnitude images, PRF thermometry relies on the measurement of the phase images.

In the recently released Philips Sonalleve MR-HIFU (Magnetic Resonance High Intensity Focused Ultrasound) product for the ablation of uterine fibroids, a gradient echo multishot EPI pulse sequence is used, with TE=20 ms, and dynamic imaging time of about 3 sec for 6 slices (3 coronal target region slices, 1 sagittal monitoring the beam path, 2 coronal slices placed near sensitive structures such as the skin, and e.g. colon) and 1 coronal with a spatial resolution of 2.5× 2.5×7 mm3. Although this is acceptable, ideally a larger spatial coverage with higher spatial resolution would be preferred, optimally isotropic 3D. But in order to ensure a safe ablation procedure, the temporal resolution should preferably remain on the order of a few seconds without compromising SNR (Signal to Noise Ratio) as this is directly proportional to the temperature accuracy. Therefore, there is a need for faster phase imaging. Embodiments of the invention may provide for faster phase imaging as well as other advantages.

In MR-HIFU the acoustic beam path (from the transducer to the target) is preferably unobstructed. This means that conventional coil elements should not be placed in an area you wish to sonicate through. This restricts coil design significantly on the anterior side of the patient, since the patient lies on her abdomen in many uterine fibroid platforms and the ultrasound enters through the abdominal wall. Therefore, the phased array coil for MR-HIFU has only limited ability for partially parallel imaging and high acceleration factor will degrade image quality.

Limited coverage of the near real-time MR monitoring methods typically used today have some disadvantages: (i) The temperature information is available on the limited volume. (ii) The size and shape of the heating focus is only partly visible, resulting incomplete information of the thermal dose and inflicted damage to the target but also of potential damage to healthy tissues (iii) Motion easily induces phase or magnitude errors in the temperature monitoring images. With true uncorrupted 3D information those errors could more easily be corrected with motion correction SW.

The imaging time is a limitation of the conventional methods. Increased speed would improve the safety and monitoring capabilities in the present applications. For future applications with e.g. more moving objects improved speed may be crucial.

In some embodiments of the invention, methods are proposed that provide high acceleration factor without significant degradation of image quality, thus addressing directly to the disadvantages of the conventional methods mentioned above. The common denominator of these methods is that they all rely on that there is relatively little change in between subsequently acquired monitoring images and only acquire part of the k-space at each dynamic. There is thus a large redundancy in the data and/or parts of the data can be inherited from previous dynamic frames.

Images for temperature mapping have very similar magnitude. Actually, if there is no motion, the magnitudes of all time frames should be same except for in a heated region where signal intensity will change due to changes in relaxation times. The heated region may be considered to be a region whose temperature has changed sufficiently such that the temperature related changes in the relaxation times affects the signal intensity. In some cases the change in temperature may be caused by a change in the location of the ultrasound focus (i.e., where the temperature can increases by more than 20 degrees celsius). However, the heated region may not necessarily be limited to a directly heated region, but may also refer to other regions. For example, it is also to observe the possible (but typically smaller) temperature changes elsewhere (with smaller signal changes).

Also, if there are large temperature differences within a voxel, then the induced phase differences between the spins might cause partial cancellation of the signal and affect the signal intensity. This is similar to an out-phase condition between fat and water spins. The maintenance of the signal magnitude can be utilized used in the proposed solution.

In one embodiment of the invention there are two essential features of the first method proposed:

1. Image ratio constrained reconstruction (IRCR) is used to approximate the to-be reconstructed image using a baseline image and a low resolution version of the to-be reconstructed image. Using the magnitude and/or phase of the result of IRCR as a constraint, and the result (both magnitude and phase) of the IRCR as initialization, to approximate the unacquired high frequency information with the acquired low frequency information. The baseline image is more completely sampled in k-space than the low resolution of the to be reconstructed image.

a. In one version, the heated region can be removed from the constraint b. In another version, the baseline drift is modeled for the current to-be reconstructed image based on that of previous reconstructed phase images 2. Partially parallel imaging (PPI), and/or partial Fourier reconstruction, can be used to improve the acquisition speed.

In a second embodiment, the data redundancy is utilized and is based on a compressed sensing approach. All methods of thermometry, not just PRF, measure the temperature related change in a parameter (directly or indirectly). The result is a phase difference image (PRF thermometry) or magnitude difference image (relaxation constant or PD thermometry) or alternatively a MR parameter map difference image (e.g., from two Look-Locker based T1 relaxation constant maps obtained at different instances in time). In the absence of motion, these difference images are sparse in image space. In fact, only the heated region that has a non-zero signal (in theory at least). Therefore, constraints of sparsity can be used to reconstruct high resolution image with only partially acquired data.

Preferably, the HIFU system should utilize coil solution allowing partial imaging methods. Generally that means that there are several coil elements with essentially different spatial sensitivity within the volume of interest. These partial imaging methods can be used in combination with the methods described below further boosting the image acceleration.

Embodiments of the invention may be useful for improving the temporal and spatial resolution, and spatial coverage of temperature mapping for any thermal therapy modality, including HIFU, RF, microwave, cryo, and laser therapy. Examples of thermal therapies are ablation, and hyper- or hypothermia. Hyperthermia may e.g. be used for localized drug delivery or gene therapy.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses a interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

Magnetic resonance data may comprise the measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonant frequency.

The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-star weighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonant frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical apparatus comprising a magnetic resonance imaging system for acquiring magnetic resonance data. The medical apparatus further comprises a processor for controlling the medical apparatus. The apparatus further comprises a memory containing machine-readable instructions for execution by the processor.

Execution of the instructions causes the processor to acquire baseline magnetic resonance data. The processor may acquire magnetic resonance data by sending instructions or control signals to the magnetic resonance imaging system which cause it to acquire magnetic resonance data. Execution of the instructions further causes the processor to reconstruct a first image using the baseline magnetic resonance data. Execution of the instructions further causes the processor to acquire under-sampled magnetic resonance data. The under-sampled magnetic resonance data is under-sampled in k-space in comparison to the baseline magnetic resonance data. In other words the under-sampled magnetic resonance data does not sample as many points in k-space as was sampled for the baseline magnetic resonance data. The under-sampled magnetic resonance data may also be referred to as sparsely sampled magnetic resonance data.

Execution of the instructions further causes the processor to reconstruct a second image using the under-sampled magnetic resonance data and the first image. As the under-sampled magnetic resonance data samples fewer points in k-space the first image is used to at least partially reconstruct the second image. This is advantageous because using data from the first image allows the second image to be reconstructed using the under-sampled magnetic resonance data. Because fewer points are sampled in k-space when acquiring the under-sampled magnetic resonance data it takes less time to acquire the under-sampled magnetic resonance data than the baseline magnetic resonance data.

Execution of the instructions further causes the processor to calculate a temperature map using the second image. In some embodiments the temperature map is calculated using both the second image and the first image. The second image is reconstructed using an image ratio constrained reconstruction algorithm. For instance the first image may be a calibration or baseline image. The temperature map may then be constructed to map a temperature change with respect to when the second image and the first image were acquired. In some embodiments the magnetic resonance data is acquired from a subject located within an imaging zone of the magnetic resonance imaging system.

As used herein an image ratio constrained reconstruction (IRCR) algorithm refers to algorithms which use an image ratio for reconstruction and also magnitude and/or phase constraints.

Examples of how an IRCR algorithm may be constructed are outlined below:
1. Acquisition
   a. before HIFU sonication, one or two full k-space baseline data sets are acquired;
   b. during HIFU sonication, partial k-space data with a fully acquired centre region are acquired for phase imaging. Not all embodiments use HIFU sonication.
2. Reconstruction Model
   a. Image ratio constrained reconstruction (IRCR):
   The fully acquired k-space data RK (usually the first time frame) is used as the reference data set. PK is the set (or sets) of partially acquired k-space data of time frame t. With the same undersampling scheme as the one for PK, a set of partial k-space data PRK can be generated from RK. Let $I_{PK}$, $I_{RK}$, and $I_{PRK}$ be images generated with PK, RK, and PRK correspondingly. Then the reconstructed image $I_{Rec}=I_{PK} \div I_{PRK} \times I_{RK}$, where $\times$ and $\div$ denote pixel-wise multiplication and division respectively. To avoid singularity, a specific threshold can be chosen before division.

b. Magnitude and/or phase constrained reconstruction: The reconstruction model is $$\min_I E[I] = \min_I \sum_{j=1}^{Nch} \|F_p(S_j I) - k_j\|_2^2 + \alpha^2 \||I| - |\bar{I}|\|_2^2, \quad [1],$$

where I is the to-be reconstructed image, $\bar{I}$ is the image reconstructed by IRCR, j is the coil count, Nch is the number of coil elements, $k_j$ is the partially acquired k-space data. $S_j$ is the sensitivity map of the $j^{th}$ coil element, $\alpha$ is a positive parameter to balance these two terms, $|*|$ is the absolute value, and $\|*\|_2$ denote the $L_2$ norm.

c. The fully acquired centre k-space data can be partially acquired, such as asymmetric in k-space or equally spaced with SENSE factor>1, and partial Fourier technique [5] or PPI [1, 2] can be applied to approximate partial unacquired data.

d. An alternative reconstruction model could use image support reduction and sparsity constraint for reconstruction. First, the partially acquired data could subtract the result of IRCR in k-space to produce the residual partially acquired data, which corresponds to an image with sparse image support (ideally, only the region with changed phase). And the reconstruction model is $$\min_{\tilde{I}} E[\tilde{I}] = \min_{\tilde{I}} \sum_{j=1}^{Nch} \|F_p(S_j \tilde{I}) - \bar{k}_j\|_2^2 + \alpha^2 \|\tilde{I}\|_{L1}, \quad [2],$$

where $\tilde{I}$ is the to-be reconstructed image, j is the coil count, Nch is the number of coil elements, $\bar{k}_j$ is the residual partially acquired k-space data. In k-space, each time frame subtract the baseline data at acquired location to produce a set of residual k-space data e. Alternatively, the heated region is removed from the magnitude/phase constraint in Eq. [1] since the phase and magnitude (although magnitude only slightly and in only a few voxels) are known to vary in this region f. If a phase constraint is used, then estimate the baseline drift of the phase in the current image based on the phase drift rate of previous images and the phase drift of the centre k-space acquired data 3. Numerical Algorithm
   a. Eq. [1] can be numerically solved using projection onto convex set (POCS). This numerical scheme is fast, and does not need parameter $\alpha$.
   b. Eq. [1] can also be solved using conjugate gradient based method. This numerical scheme could be slightly more accurate, but takes longer reconstruction time and several carefully chosen parameters.

In another embodiment the medical apparatus further comprises a temperature treatment system for treating a target volume of a subject. In some embodiments the target volume is within an imaging zone of the magnetic resonance imaging system. Execution of the instructions further causes the processor to treat the target volume during acquisition of the under-sampled magnetic resonance data. For instance the processor may treat the target volume by generating temperature treatment system commands in accordance with the temperature map. The processor may further cause the target volume to be treated by sending the temperature treatment system commands to the temperature treatment system. As used herein the temperature treatment system commands comprise instructions or control signals which the processor uses to control the temperature treatment system. A temperature treatment system as used herein comprises a system for controllably raising or lowering the temperature of the target volume within the subject.

This embodiment is advantageous because the under-sampled magnetic resonance data can be acquired extremely rapidly. This facilitates the rapid calculation of the temperature map using the second image. The temperature map may be used as a feedback for controlling the temperature treatment system.

In another embodiment execution of the instructions further causes the processor to select k-space sampled points for the acquisition of the under-sampled magnetic resonance data in accordance with the location of the target volume. For instance the k-space sample points are locations which have the strongest correlation with the location of the target volume and the second image can be selected. This is advantageous because if the target volume is either being heated or cooled then one would expect that the image data used to generate a temperature map will be changing most greatly within the target volume.

The selecting of k-sample points or areas is known in literature as selecting a region of interest by using region of interest information to determine k-space trajectories which avoid the acquisition of redundant information during dynamic imaging. Likewise the use of a region of interest in selecting k-space sample trajectories is known for suppressing signals external to a region of interest in magnetic resonance imaging also. Using known techniques the k-space sample points which have the strongest correlation with the target volume in the second image can be selected.

One conventional scheme is to use single value decomposition (SVD) analysis to the k-space corresponding to a region of interest or in this case the target volume. This embodiment is particularly advantageous because the k-space sample points are selected such that the region of the second image corresponding to the target volume is better reconstructed by the k-space sample points than the surrounding or remaining portion of the second image. This may aid in accelerating the acquisition of the under-sampled magnetic resonance data.

In another embodiment execution of the instructions further cause the processor to repeatedly acquire the under-sampled magnetic resonance data. Execution of the instructions further causes the processor to repeatedly reconstruct the second image using the under-sampled magnetic resonance data and the first image. Execution of the instructions further causes the processor to repeatedly calculate a temperature map using the second image. In some embodiments the first image is also used to calculate the temperature map. Execution of the instructions further causes the processor to repeatedly generate temperature treatment system commands in accordance with the temperature map. Execution of the instructions further causes the processor to repeatedly send the temperature treatment system commands to the temperature treatment system. This embodiment is advantageous because the under-sampled magnetic resonance data is used to generate a temperature map which is used for feedback control of the temperature treatment system.

In another embodiment the temperature treatment system is a high-intensity focused ultrasound system.

In another embodiment the temperature treatment system is a radio-frequency tissue treating system. For instance a radio-frequency antenna may be used to heat the target volume using radio-frequency energy. Typically an additional antenna is used or placed in the vicinity of the subject to generate the radio-frequency energy that heats the target zone.

In another embodiment the temperature treatment system is a microwave applicator. A microwave applicator is adapted for directing microwave energy at the target zone. This may cause an increase in temperature of the target zone.

In another embodiment the temperature treatment system is a cryo-ablator. A cryo-ablator is adapted for cooling the target zone or a portion of the target zone to temperatures which cause the ablation of tissue.

In another embodiment the temperature treatment system is a laser. The laser may be used to selectively ablate tissue.

In another embodiment the location of the target volume is used as a constraint during reconstruction of the second image.

In another embodiment the first image is a phase image. The second image is a phase image. The thermal map is calculated by determining a phase shift between voxels of the first image and voxels of the second image. In this embodiment the temperature map is constructed using a gradient-recalled echo (GRE) imaging sequence to measure the phase change resulting from the temperature change between the first image and the second image. The phase change occurs due to the temperature-dependent change in the resonant frequency.

In another embodiment the first and second image are used to construct the thermal map by calculating a change in the proton density.

In another embodiment the first and second image are used to construct the thermal map by calculating a change in the T1 relaxation time of water protons.

In another embodiment the first and second image are used to construct the thermal map by calculating a change in the T2 relaxation time of water protons.

In another embodiment the first and second image are used to construct the thermal map by calculating a change in the T2-star relaxation times of water protons.

In another embodiment the first image and the second image are used to construct the thermal map by calculating a change in the change of a diffusion constant.

In another embodiment the change is calculated for each voxel of the second image.

in another embodiment, the image ratio constrained reconstruction algorithm comprises calculating a constraint, wherein the constraint is calculated on any one of the following: a magnitude image, a phase image, a complex image, and combinations thereof. The magnitude image, the phase image, the complex image, may refer to the first image and/or the second image.

In another embodiment the baseline magnetic resonance data and the under-sampled magnetic resonance data is acquired and/or reconstructed using a parallel imaging technique. For instance the SENSE or GRAPPA techniques may be used.

In another embodiment the baseline magnetic resonance data and the under-sampled magnetic resonance data is acquired using a two-dimensional or a three-dimensional gradient echo pulse sequence.

In another embodiment the baseline magnetic resonance data and the under-sampled magnetic resonance data is acquired with a two-dimensional or a three-dimensional gradient echo EPI pulse sequence. k-space sample points for the acquisition of the under-sampled magnetic resonance data and the baseline magnetic resonance data are chosen such that the first image and the second image are acquired using similar echo times. In other words the echo times used to acquire the first image and the second image are the same duration plus or minus a predetermined amount of time. One can calculate spin frequency images from the phase images using the separate echo times. It is the different in the frequency that determines the temperature change.

The baseline magnetic resonance data and the under-sampled magnetic resonance data are acquired using a two-dimensional or a three-dimensional spin echo or turbo spin echo pulse sequence.

In another aspect the invention provides for a method of operating a medical apparatus. Likewise the invention also provides for a computer-implemented method. The medical apparatus comprises a magnetic resonance imaging system for acquiring magnetic resonance data. The method comprises the step of acquiring baseline magnetic resonance data. The magnetic resonance imaging system may be used for acquiring the baseline magnetic resonance data. The method further comprises the step of reconstructing a first image using the baseline magnetic resonance data. Standard image reconstruction techniques may be used for reconstructing the first image.

The method further comprises the step of acquiring under-sampled magnetic resonance data. Again the magnetic resonance imaging system may be used for acquiring the under-sampled magnetic resonance data. The under-sampled magnetic resonance data is under-sampled in k-space in comparison to the baseline magnetic resonance data. The method further comprises the step of reconstructing a second image using the under-sampled magnetic resonance data and the first image. The second image is reconstructed using an image ratio constrained reconstruction algorithm. The method further comprises the step of calculating a temperature map using the second image.

In another aspect the invention provides for a computer program product comprising machine executable instructions for execution by a processor of a medical apparatus. For instance the computer program product may be stored on a computer-readable storage medium. The medical apparatus comprises a magnetic resonance imaging system for acquiring magnetic resonance data. Execution of the instructions further causes the processor to acquire baseline magnetic resonance data. Execution of the instructions further causes the processor to reconstruct a first image using the baseline magnetic resonance data.

Execution of the instructions further causes the processor to acquire under-sampled magnetic resonance data. The under-sampled magnetic resonance data is under-sampled in k-space in comparison to the baseline magnetic resonance data. Execution of the instructions further causes the processor to reconstruct a second image using the under-sampled magnetic resonance data and the first image. The second image is reconstructed using an image ratio constrained reconstruction algorithm. Execution of the instructions further causes the processor to calculate a temperature map using the second image.

In one aspect the invention provides for a medical apparatus comprising a magnetic resonance imaging system for acquiring magnetic resonance data. The medical apparatus further comprises a processor for controlling the medical apparatus. The apparatus further comprises a memory containing machine-readable instructions for execution by the processor.

Execution of the instructions causes the processor to acquire baseline magnetic resonance data. The processor may acquire magnetic resonance data by sending instructions or control signals to the magnetic resonance imaging system which cause it to acquire magnetic resonance data. Execution of the instructions further causes the processor to reconstruct a first image using the baseline magnetic resonance data. Execution of the instructions further causes the processor to acquire under-sampled magnetic resonance data. The under-sampled magnetic resonance data is under-sampled in k-space in comparison to the baseline magnetic resonance data. In other words the under-sampled magnetic resonance data does not sample as many points in k-space as was sampled for the baseline magnetic resonance data. The under-sampled magnetic resonance data may also be referred to as sparsely sampled magnetic resonance data.

Execution of the instructions further causes the processor to reconstruct a second image using the under-sampled magnetic resonance data and the first image. The second image is reconstructed using compressed sensing. Embodiments may use a compressed sensing algorithm with the first image and the under-sampled magnetic resonance data as inputs for the algorithm. As the under-sampled magnetic resonance data samples fewer points in k-space the first image is used to at least partially reconstruct the second image. This is advantageous because using data from the first image allows the second image to be reconstructed using the under-sampled magnetic resonance data. Because fewer points are sampled in k-space when acquiring the under-sampled magnetic resonance data it takes less time to acquire the under-sampled magnetic resonance data than the baseline magnetic resonance data.

Examples of compressed sensing algorithms are outlined below:
1. Acquisition
   a. Each dynamic level is sub-sampled using a variable density pseudo random pattern though such that each dynamic level has an equal amount of randomly distributed samples
      i. The samples can also be constrained as explained in Ref. 3 to further reduce aliasing
2. Reconstruction Model
   a. Sparsity in image space is used as the regularization term. Examples of possible regularization include: total variation, wavelet transform, non-convex finite difference, trained dictionary, non-local mean, and others.
   b. One possible reconstruction model is:

$$\min_{\bar{I}} E[\bar{I}] = \min_{\bar{I}} \sum_{j=1}^{Nch} \|F_p(S_j\bar{I}) - \bar{k}_j\|_2^2 + \lambda\Psi(\bar{I}),,$$

where $\bar{I}$ is the to-be reconstructed image, j is the coil count, Nch is the number of coil elements, $\bar{k}_j$ is the residual partially acquired k-space data, $\Psi(\bullet)$ is a sparsity constraint operator mentioned in a, $\lambda$ is an non-negative parameter to balance these two terms.
3. Numerical Methods
   a. Several methods can be employed for recovering the full image from the randomly under-sampled data, such as orthogonal marching pursuit, split Bregman, and others.

A benefit of the IRCR method as compared to compressed sensing is that it is much less computationally laborious.

Execution of the instructions further causes the processor to calculate a temperature map using the second image. In some embodiments the temperature map is calculated using both the second image and the first image. For instance the first image may be a calibration or baseline image. The temperature map may then be constructed to map a temperature change with respect to when the second image and the first image were acquired. In some embodiments the magnetic resonance data is acquired from a subject located within an imaging zone of the magnetic resonance imaging system.

In another embodiment the medical apparatus further comprises a temperature treatment system for treating a target volume of a subject. In some embodiments the target volume is within an imaging zone of the magnetic resonance imaging system. Execution of the instructions further causes the processor to treat the target volume during acquisition of the under-sampled magnetic resonance data. For instance the processor may treat the target volume by generating temperature treatment system commands in accordance with the temperature map. The processor may further cause the target volume to be treated by sending the temperature treatment system commands to the temperature treatment system. As used herein the temperature treatment system commands comprise instructions or control signals which the processor uses to control the temperature treatment system. A temperature treatment system as used herein comprises a system for controllably raising or lowering the temperature of the target volume within the subject.

This embodiment is advantageous because the under-sampled magnetic resonance data can be acquired extremely rapidly. This facilitates the rapid calculation of the temperature map using the second image. The temperature map may be used as a feedback for controlling the temperature treatment system.

In another embodiment execution of the instructions further causes the processor to select k-space sampled points for the acquisition of the under-sampled magnetic resonance data in accordance with the location of the target volume. For instance the k-space sample points are locations which have the strongest correlation with the location of the target volume and the second image can be selected. This is advantageous because if the target volume is either being heated or cooled then one would expect that the image data used to generate a temperature map will be changing most greatly within the target volume.

The selecting of k-sample points or areas is known in literature as selecting a region of interest by using region of interest information to determine k-space trajectories which avoid the acquisition of redundant information during dynamic imaging. Likewise the use of a region of interest in selecting k-space sample trajectories is known for suppressing signals external to a region of interest in magnetic resonance imaging also. Using known techniques the k-space sample points which have the strongest correlation with the target volume in the second image can be selected.

One conventional scheme is to use single value decomposition (SVD) analysis to the k-space corresponding to a region of interest or in this case the target volume. This embodiment is particularly advantageous because the k-space sample points are selected such that the region of the second image corresponding to the target volume is better reconstructed by the k-space sample points than the surrounding or remaining portion of the second image. This may aid in accelerating the acquisition of the under-sampled magnetic resonance data.

In another embodiment execution of the instructions further cause the processor to repeatedly acquire the under-sampled magnetic resonance data. Execution of the instructions further causes the processor to repeatedly reconstruct the second image using the under-sampled magnetic resonance data and the first image. Execution of the instructions further causes the processor to repeatedly calculate a temperature map using the second image. In some embodiments the first image is also used to calculate the temperature map. Execution of the instructions further causes the processor to repeatedly generate temperature treatment system commands in accordance with the temperature map. Execution of the instructions further causes the processor to repeatedly send the temperature treatment system commands to the temperature treatment system. This embodiment is advantageous because the under-sampled magnetic resonance data is used to generate a temperature map which is used for essentially feedback control of the temperature treatment system.

In another embodiment the temperature treatment system is a high-intensity focused ultrasound system.

In another embodiment the temperature treatment system is a radio-frequency tissue treating system. For instance a radio-frequency antenna may be used to heat the target volume using radio-frequency energy. Typically an additional antenna is used or placed in the vicinity of the subject to generate the radio-frequency energy that heats the target zone.

In another embodiment the temperature treatment system is a microwave applicator. A microwave applicator is adapted for directing microwave energy at the target zone. This may cause an increase in temperature of the target zone.

In another embodiment the temperature treatment system is a cryo-ablator. A cryo-ablator is adapted for cooling the target zone or a portion of the target zone to temperatures which cause the ablation of tissue.

In another embodiment the temperature treatment system is a laser. The laser may be used to selectively ablate tissue.

In another embodiment a seed image for the reconstruction of the second image using compressed sensing is calculated using an image ratio constrained reconstruction algorithm. This embodiment is advantageous because this allows the compressed sensing algorithm to more rapidly converge to a solution. This speeds up the overall construction of the second image when compressed sensing is used.

In another embodiment the first image is a phase image. The second image is a phase image. The thermal map is calculated by determining a phase shift between voxels of the first image and voxels of the second image. In this embodiment the temperature map is constructed using a gradient-recalled echo (GRE) imaging sequence to measure the phase change resulting from the temperature change between the first image and the second image. The phase change occurs due to the temperature-dependent change in the resonant frequency.

In another embodiment the first and second image are used to construct the thermal map by calculating a change in the proton density.

In another embodiment the first and second image are used to construct the thermal map by calculating a change in the T1 relaxation time of water protons.

In another embodiment the first and second image are used to construct the thermal map by calculating a change in the T2 relaxation time of water protons.

In another embodiment the first and second image are used to construct the thermal map by calculating a change in the T2-star relaxation times of water protons.

In another embodiment the first image and the second image are used to construct the thermal map by calculating a change in the change of a diffusion constant.

In another embodiment the change is calculated for each voxel of the second image.

In another embodiment the baseline magnetic resonance data and the under-sampled magnetic resonance data is acquired and/or reconstructed using a parallel imaging technique. For instance the SENSE or GRAPPA techniques may be used.

In another embodiment the baseline magnetic resonance data and the under-sampled magnetic resonance data is acquired using a two-dimensional or a three-dimensional gradient echo pulse sequence.

In another embodiment the baseline magnetic resonance data and the under-sampled magnetic resonance data is acquired with a two-dimensional or a three-dimensional gradient echo EPI pulse sequence. k-space sample points for the acquisition of the under-sampled magnetic resonance data and the baseline magnetic resonance data are chosen such that the first image and the second image are acquired using a similar echo time. In other words the echo times used to acquire the first image and the second image are the same duration plus or minus a predetermined amount of time. In some embodiments the echo time of the first image and the second image are identical. One can calculate spin frequency images from the phase images using echo times which are different. It is the difference in the frequency that determines the temperature change. In some embodiments the echo time of the first image and the second image are identical. One can calculate spin frequency images from the phase images using echo times which are different. It is the difference in the frequency that determines the temperature change.

The baseline magnetic resonance data and the under-sampled magnetic resonance data are acquired using a two-dimensional or a three-dimensional spin echo or turbo spin echo pulse sequence.

In another aspect the invention provides for a method of operating a medical apparatus. Likewise the invention also provides for a computer-implemented method. The medical apparatus comprises a magnetic resonance imaging system for acquiring magnetic resonance data. The method comprises the step of acquiring baseline magnetic resonance data. The magnetic resonance imaging system may be used for acquiring the baseline magnetic resonance data. The method further comprises the step of reconstructing a first image using the baseline magnetic resonance data. Standard image reconstruction techniques may be used for reconstructing the first image.

The method further comprises the step of acquiring under-sampled magnetic resonance data. Again the magnetic resonance imaging system may be used for acquiring the under-sampled magnetic resonance data. The under-sampled magnetic resonance data is under-sampled in k-space in comparison to the baseline magnetic resonance data. The method further comprises the step of reconstructing a second image using the under-sampled magnetic resonance data and the first image. The second image is reconstructed using compressed sensing. The method further comprises the step of calculating a temperature map using the second image.

In another aspect the invention provides for a computer program product comprising machine executable instructions for execution by a processor of a medical apparatus. For instance the computer program product may be stored on a computer-readable storage medium. The medical apparatus comprises a magnetic resonance imaging system for acquiring magnetic resonance data. Execution of the instructions further causes the processor to acquire baseline magnetic resonance data. Execution of the instructions further causes the processor to reconstruct a first image using the baseline magnetic resonance data.

Execution of the instructions further causes the processor to acquire under-sampled magnetic resonance data. The under-sampled magnetic resonance data is under-sampled in k-space in comparison to the baseline magnetic resonance data. Execution of the instructions further causes the processor to reconstruct a second image using the under-sampled magnetic resonance data and the first image. The second image is reconstructed using compressed sensing. Execution of the instructions further causes the processor to calculate a temperature map using the second image.

In another aspect the invention provides for a medical apparatus comprising a magnetic resonance imaging system for acquiring magnetic resonance data. Embodiments of the previously described medical apparatus may also apply to this medical apparatus. The medical apparatus further comprises a processor for controlling the medical apparatus. The medical apparatus further comprises a memory containing machine-readable instructions for execution by the processor. Execution of the instructions causes the processor to acquire baseline magnetic resonance data. Execution of the instructions further causes the processor to reconstruct a baseline phase image using the baseline magnetic resonance data. The baseline phase image corresponds to the first image of the previously described medical apparatus. Execution of the instructions further causes the processor to acquire under-sampled magnetic resonance data. The under-sampled magnetic resonance data is under-sampled in k-space in comparison to the baseline magnetic resonance data. Execution of the instructions further causes the processor to reconstruct a phase image using the under-sampled magnetic resonance data and the baseline phase image. The phase image as herein described is equivalent to the second image of a previously described medical apparatus. Embodiments of this invention are advantageous because phase images may be acquired rapidly and used for such things as creating temperature maps or as data for a feedback loop which controls an apparatus.

In another embodiment execution of the instructions further causes the processor to calculate a temperature map using the phase image. In some embodiments the baseline phase image is also used to at least partially calculate the temperature map. For instance the change in phase between the baseline phase image and the phase image may be used to calculate the temperature.

In another embodiment the medical apparatus further comprises a temperature treatment system for treating a target volume of a subject. Execution of the instructions further causes the processor to treat the target volume during acquisition of the under-sampled magnetic resonance data.

In another embodiment execution of the instructions further causes the processor to select k-space sample points for the acquisition of the under-sampled magnetic resonance data in accordance with the location of the target volume.

In another embodiment execution of the instructions further cause the processor to repeatedly acquire the under-sampled magnetic resonance data. Execution of the instructions further causes the processor to reconstruct the phase image using the under-sampled magnetic resonance data and the baseline phase image. Execution of the instructions further causes the processor to repeatedly calculate a temperature map using the phase image. Execution of the instructions further causes the processor to repeatedly generate temperature treatment system commands in accordance with the temperature map. Execution of the instructions further causes the processor to repeatedly send the temperature treatment system commands to the temperature treatment system.

In another embodiment the temperature treatment system is a high-intensity focused ultrasound system.

In another embodiment the temperature treatment system is a radio-frequency tissue treating system.

In another embodiment the temperature treatment system is a microwave applicator.

In another embodiment the temperature treatment system is a cryo-ablator.

In another embodiment the temperature treatment system is a laser.

In another embodiment the phase image is reconstructed using an image ratio constrained reconstruction algorithm.

In another embodiment the phase image is reconstructed using compressed sensing.

In another embodiment a seed phase image for the compressed sensing is calculated using an image ratio constrained reconstruction algorithm.

In another embodiment the thermal map is reconstructed using a keyhole algorithm.

In another embodiment the under-sampled magnetic resonance data is acquired repeatedly. The phase image is acquired repeatedly using the repeatedly acquired under-sampled magnetic resonance data.

In another aspect the invention provides for a method of operating the medical apparatus. The medical apparatus comprises a magnetic resonance imaging system for acquired magnetic resonance data. The method comprises the step of acquiring the baseline magnetic resonance data. The method further comprises the step of reconstructing a baseline phase image using the baseline magnetic resonance data. The method further comprises the step of acquiring under-sampled magnetic resonance data. The under-sampled magnetic resonance data is under-sampled in k-space in comparison to the baseline magnetic resonance data. The method further comprises the step of reconstructing a phase image using the under-sampled magnetic resonance data and the baseline phase image. This method may also be implemented as a computer-implemented method.

In another aspect the invention provides for a computer program product comprising machine executable instructions for execution by a processor which controls a medical apparatus. The computer program product may for instance be stored on a computer-readable storage medium. Execution of the instructions causes the processor to acquire baseline magnetic resonance data. The magnetic resonance imaging system may be used for acquiring the baseline magnetic resonance data. Execution of the instructions further causes the processor to reconstruct a baseline phase image using the baseline magnetic resonance data. Execution of the instructions further causes the processor to acquire under-sampled magnetic resonance data. The under-sampled magnetic resonance data is under-sampled in k-space in comparison to the baseline magnetic resonance data. Execution of the instructions further causes the processor to reconstruct a phase image using the under-sampled magnetic resonance data and the baseline phase image.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
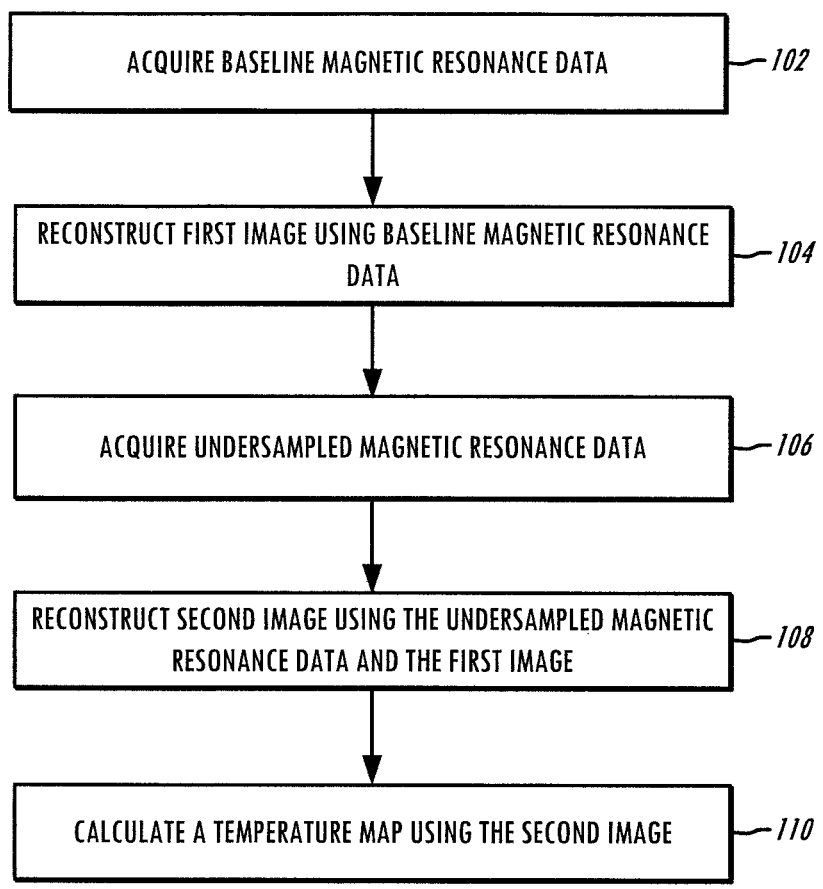
FIG. 1 shows a flowchart which illustrates an embodiment of a method according to the invention.

FIG. 1 shows a flowchart which illustrates an embodiment of a method according to the invention. In step 102 baseline magnetic resonance data is acquired. In step 104 a first image is reconstructed using the baseline magnetic resonance data. In step 106 under-sampled magnetic resonance data is acquired. In step 108 a second image is reconstructed using the under-sampled magnetic resonance data and the first image. In step 110 a temperature map is calculated using the second image. In some embodiments the temperature map is calculated using both the second image and the first image.

Figure 2:
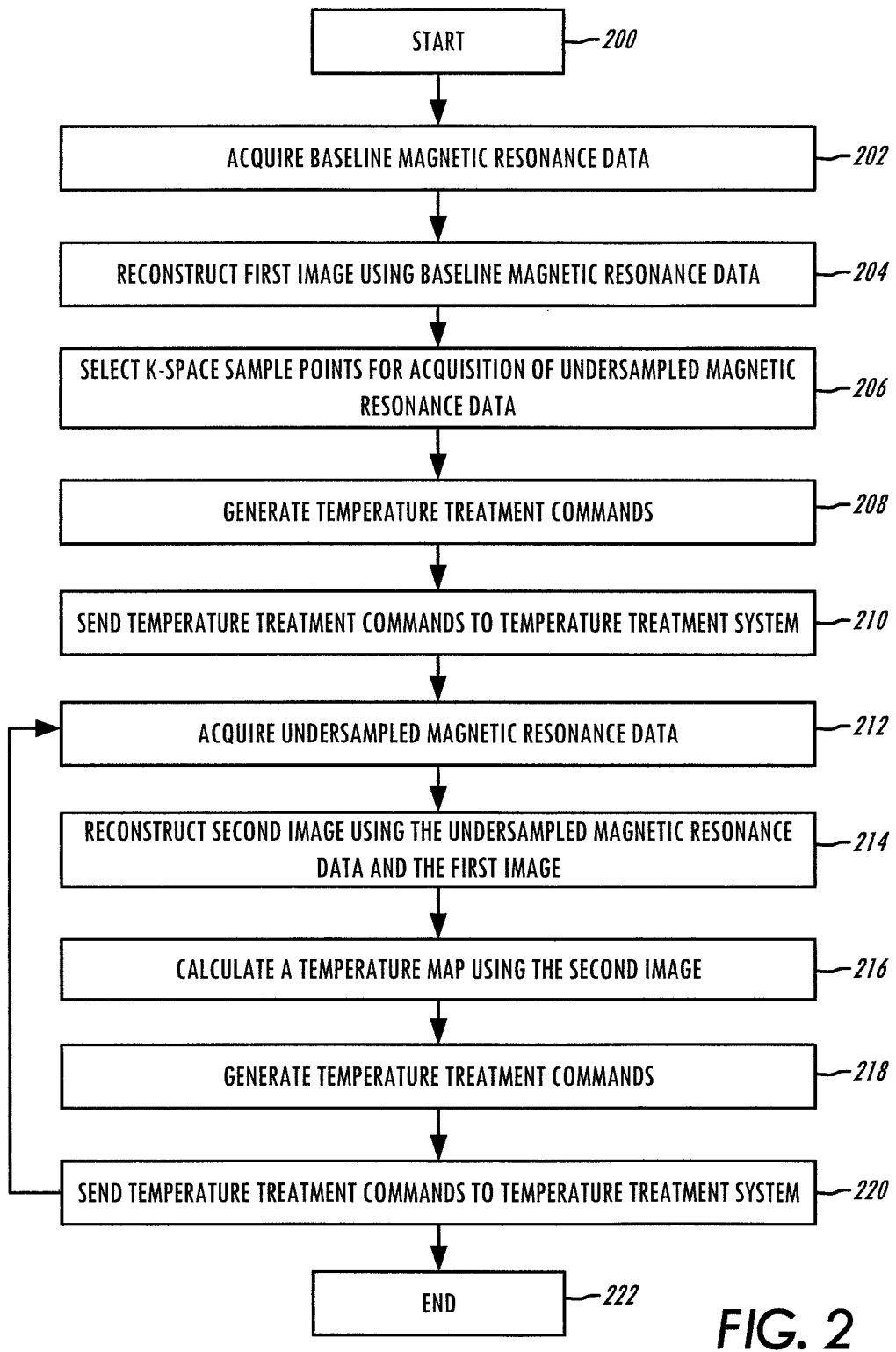
FIG. 2 shows a flowchart which illustrates a further embodiment of a method according to the invention.

FIG. 2 shows a flowchart which illustrates a method according to a further embodiment according to the invention. In step 200 the method starts. Next in step 202 baseline magnetic resonance data is acquired. In step 204 a first image is reconstructed using baseline magnetic resonance data. Next in step 206 k-space sample points are selected for acquisition of under-sampled magnetic resonance data. In step 208 temperature treatment commands are generated. In step 210 temperature treatment commands are sent to the temperature treatment system. This causes the temperature treatment system to begin temperature treatment of the target zone. In step 212 under-sampled magnetic resonance data is acquired. Next the second image is reconstructed using the under-sampled magnetic resonance data and the first image. Further in step 216 a temperature map is calculated using the second image and also possibly the first image. In step 218 temperature treatment commands are generated using the temperature map.

Next in step 220 the temperature treatment commands are sent to the temperature treatment system. The temperature treatment commands were originally sent to the temperature treatment system in step 210 but now the temperature treatment commands have been modified in accordance or using the temperature map. The system then proceeds back to step 212 and acquires more under-sampled magnetic resonance data. Then the steps are proceeded through and a replacement temperature map is calculated using the second image. Steps 212-220 form a feedback loop where the temperature map is used to modify the temperature treatment commands. For instance the temperature treatment commands may be modified in accordance with a temperature map and a treatment plan. When the temperature treatment or therapy is finished then the method ends in step 222.

Figure 3:
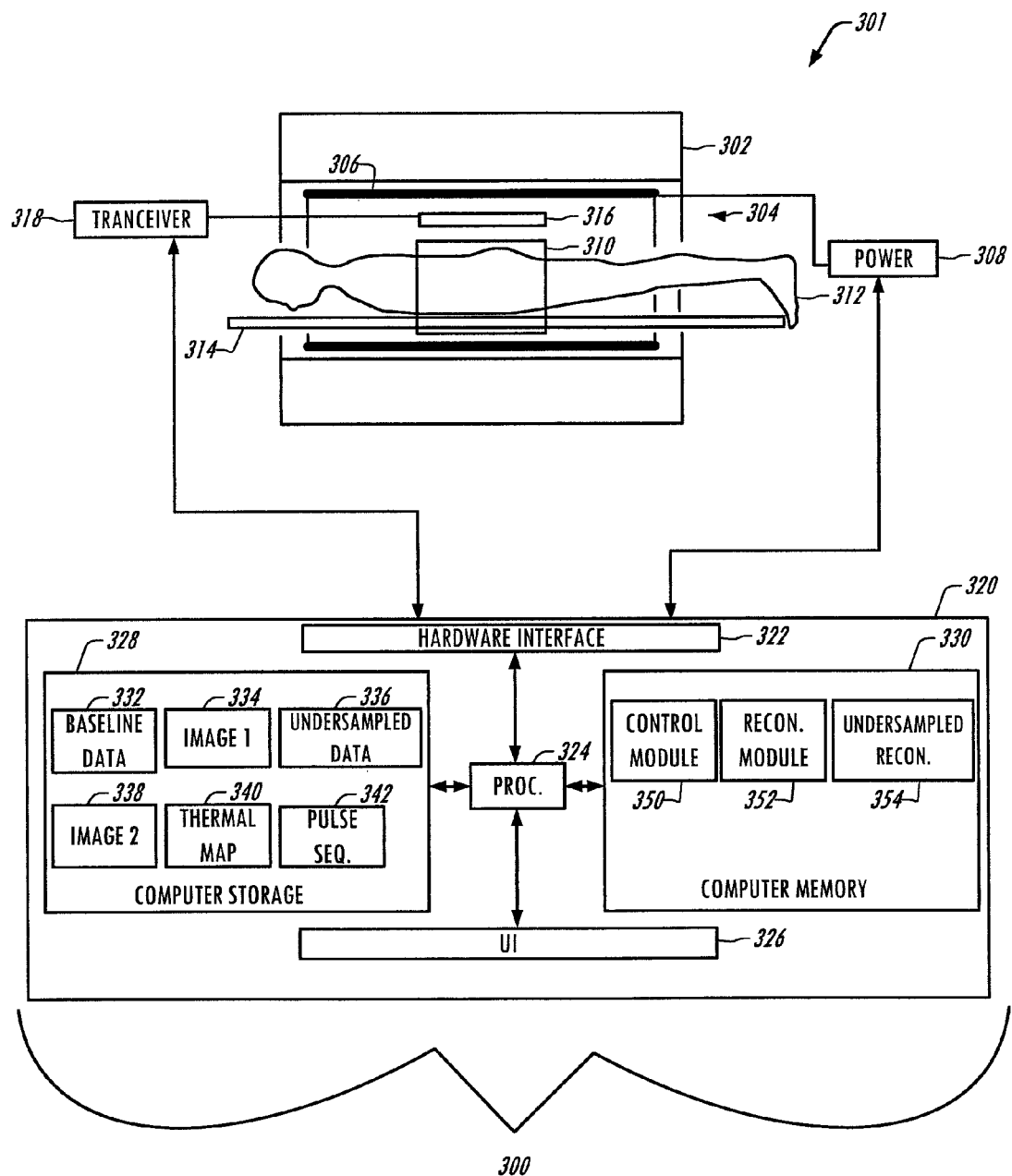
FIG. 3 illustrates a medical apparatus according to an embodiment of the invention.

FIG. 3 illustrates a medical apparatus 300 according to an embodiment of the invention. The medical apparatus comprises a magnetic resonance imaging system 301. The magnetic resonance imaging system comprises a cylindrical magnet 302. The magnet 302 has a bore 304 through it. The magnet 302 shown in FIG. 3 is a cylindrical type superconducting magnet. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 304 of the cylindrical magnet there is an imaging zone 310 where the magnetic field is strong and uniform enough to perform magnetic resonance imaging.

Inside the bore 304 is a set of magnetic field gradient coils 306. Within the bore 304 of the magnet there are magnetic field gradient coils 306 which is used for acquisition of magnetic resonance data to spatially encode magnetic spins within an imaging zone of the magnet. The magnetic field gradient coils are connected to a magnetic field gradient coil power supply 308. The magnetic field gradient coil 306 is intended to be representative. Typically magnetic field gradient coils 306 contain three separate sets of coils for spatially encoding in three orthogonal spatial directions. A magnetic field gradient power supply 308 supplies current to the magnetic field gradient coils 306. The current supplied to the magnetic field coils 306 is controlled as a function of time and may be ramped or pulsed.

A portion of a subject 312 is within the imaging zone 310. The subject 312 is reposing on a subject support 314. Adjacent to the imaging zone 310 is a radio-frequency coil 316. Adjacent to the imaging zone 310 is a radio frequency radio-frequency coil 316 for manipulating the orientations of magnetic spins within the imaging zone 310 and for receiving radio transmissions from spins also within the imaging zone 310. The radio-frequency coil 316 may contain multiple coil elements. The radio-frequency coil may also be referred to as a channel or as a radio-frequency antenna. The radio frequency coil is connected to a radio frequency transceiver 318. The radio frequency coil 316 and radio frequency transceiver 318 may be replaced by separate transmit and receive coils and a separate transmitter and receiver. It is understood that the radio frequency coil 316 and the radio frequency transceiver 318 are simply representative. The radio-frequency coil 316 is intended to also represent a dedicated transmit antenna and a dedicated receive antenna. Likewise the transceiver may also represent a separate transmitter and receivers.

The transceiver 318 and the magnetic field gradient coil power supply 308 are connected to a hardware interface 322 of a computer system 320. The hardware interface 322 is further connected to a processor 324. The processor 324 is also connected to a user interface 326, computer storage 328, and computer memory 330.

The computer storage 328 is shown as containing baseline magnetic resonance data 332. The computer storage 328 is further shown as containing a first image 334 reconstructed from the baseline magnetic resonance data 332. The computer storage 328 is shown as further containing under-sampled magnetic resonance data 336. The computer storage 328 is further shown as containing a second image 338 which has been reconstructed from the under-sampled magnetic resonance data 336 and the first image 334. The computer storage 328 is shown as further containing a thermal map 340 reconstructed from the second image 338 and possibly also reconstructed at least partially using the first image 334. The computer storage 328 is shown as further containing a pulse sequence 342. The pulse sequence 342 contains commands and timing relationships which may be used by the processor 324 to control the operation of the magnetic resonance imaging system 301 for acquiring the baseline magnetic resonance data 332 and the under-sampled magnetic resonance data 336. The computer memory 330 is shown as containing a control module 350. The control module 350 contains computer executable code which allows the processor 324 to control the operation and function of the medical apparatus 300.

The computer memory 330 is shown as further containing a reconstruction module 352. The reconstruction module contains computer executable code for reconstructing the baseline magnetic resonance data 332 into the first image 334. The computer memory 330 is shown as further containing an under-sampled reconstruction module 354. The under-sampled reconstruction module 354 contains executable code which uses the under-sampled magnetic resonance data 336 and the first image 334 to reconstruct the second image 338. In some embodiments the under-sampled reconstruction module 354 comprises computer executable instructions for implementing an image ratio constrained reconstruction algorithm. In some other embodiments the under-sampled reconstruction module 354 comprises computer executable instructions for implementing a compressed sensing reconstruction algorithm.

The computer memory 330 is shown as further containing a thermal mapping module 356 which contains computer executable code which is used for constructing or calculating the thermal map 340 using the second image 338 and also possibly the first image 334.

Figure 4:
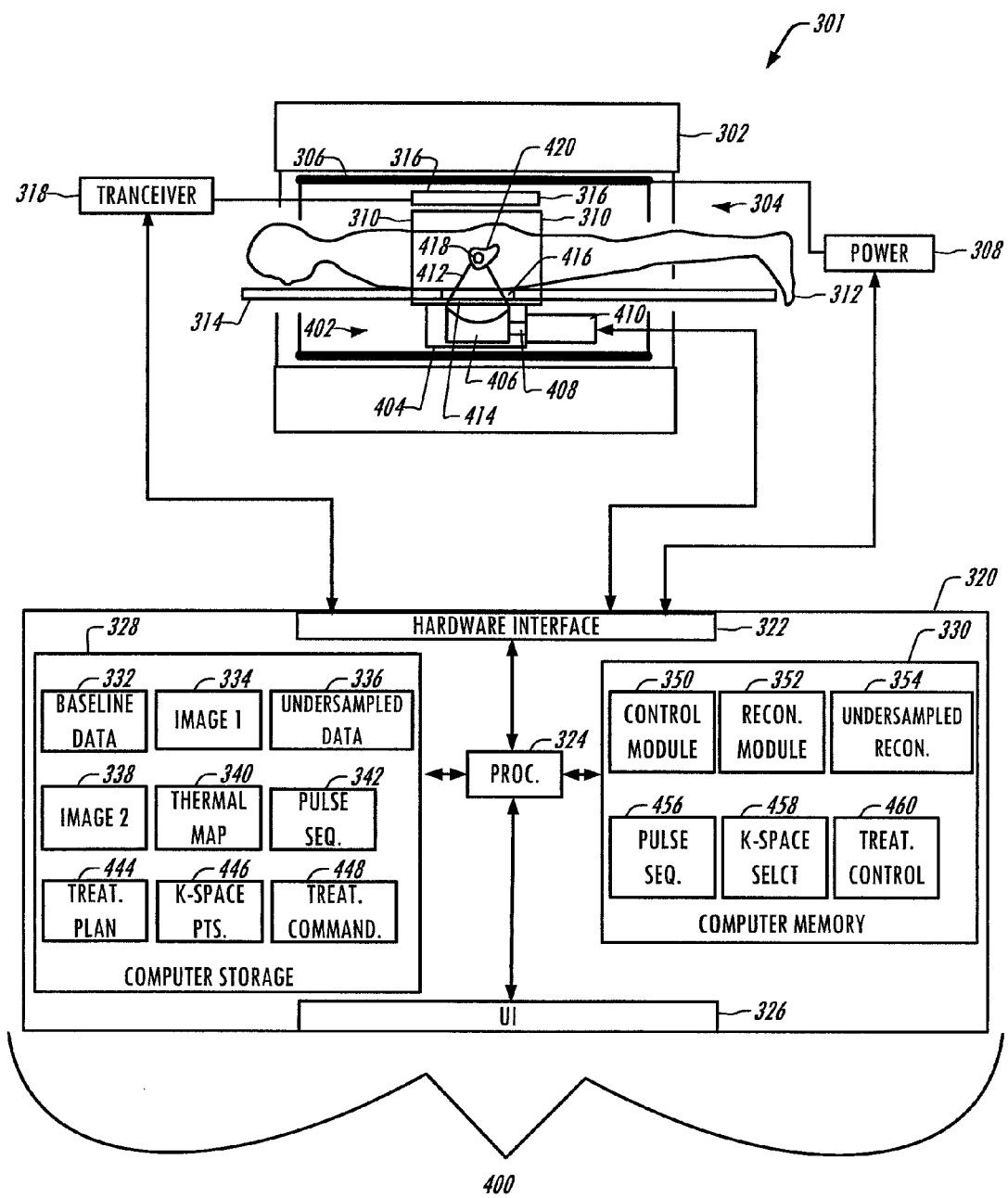
FIG. 4 illustrates a medical apparatus according to a further embodiment of the invention.

FIG. 4 illustrates a medical apparatus 400 according to a further embodiment of the invention. The embodiment shown in FIG. 4 comprises a temperature treatment system which is a high-intensity focused ultrasound system 402. The high-intensity focused ultrasound system comprises a fluid-filled chamber 404. Within the fluid-filled chamber 404 is an ultrasound transducer 406. Although it is not shown in this FIG. the ultrasound transducer 406 may comprise multiple ultrasound transducer elements each capable of generating an individual beam of ultrasound. This may be used to steer the location of a sonication point 418 electronically by controlling the phase and/or amplitude of alternating electrical current supplied to each of the ultrasound transducer elements.

The ultrasound transducer 406 is connected to a mechanism 408 which allows the ultrasound transducer 406 to be repositioned mechanically. The mechanism 408 is connected to a mechanical actuator 410 which is adapted for actuating the mechanism 408. The mechanical actuator 410 also represents a power supply for supplying electrical power to the ultrasound transducer 406. In some embodiments the power supply may control the phase and/or amplitude of electrical power to individual ultrasound transducer elements. In some embodiments the mechanical actuator/power supply 410 is located outside of the bore 304 of the magnet 302.

The ultrasound transducer 406 generates ultrasound which is shown as following the path 412. The ultrasound 412 goes through the fluid-filled chamber 408 and through an ultrasound window 414. In this embodiment the ultrasound then passes through a gel pad 416. The gel pad is not necessarily present in all embodiments but in this embodiment there is a recess in the subject support 314 for receiving a gel pad 416.

The gel pad 416 helps couple ultrasonic power between the transducer 406 and the subject 312. After passing through the gel pad 416 the ultrasound 412 passes through the subject 312 and is focused to a sonication point 418. The sonication point 418 is being focused within a target zone 420. The sonication point 418 may be moved through a combination of mechanically positioning the ultrasonic transducer 406 and electronically steering the position of the sonication point 418 to treat the entire target zone 420.

The high-intensity focused ultrasound system 402 is shown as being also connected to the hardware interference 322 of the computer system 320. The computer system 320 and the contents of its storage 328 and memory 330 are equivalent to that as shown in FIG. 3.

The computer storage 328 is shown as containing a treatment plan 444. The treatment plan 444 contains a description and/or instructions for treating the target zone 420 by the temperature treatment system 402. The treatment plan 444 may in some embodiments contain anatomical data which allows the processor 344 to register the target zone 420 to magnetic resonance images generated by the magnetic resonance imaging system 301. The computer storage 328 is shown as further containing k-space sample points. The computer storage 328 is shown as further containing temperature treatment system commands 448. The temperature treatment system commands when sent by the processor 324 to the high-intensity focused ultrasound system 402 causes it to sonicate the sonication zone 418 and also move the sonication point around the target zone 420.

The computer memory 330 is shown as containing a pulse sequence generation module and a k-space selection module 458. The k-space selection module 458 is adapted and contains computer executable code for selecting the k-space sample points 446. The k-space sample points are selected such that the target zone 420 is well represented and reconstructed by those k-space sample points. The pulse sequence generation module 456 is adapted for using the k-space sample points for generating the pulse sequences 342. The computer memory 330 is shown as further containing a temperature treatment system control module 460. The temperature treatment system control module 460 is adapted for generating the temperature treatment system commands 448. The temperature treatment system commands 448 may be generated using the treatment plan 448 and/or the thermal map 340.

Figure 5:
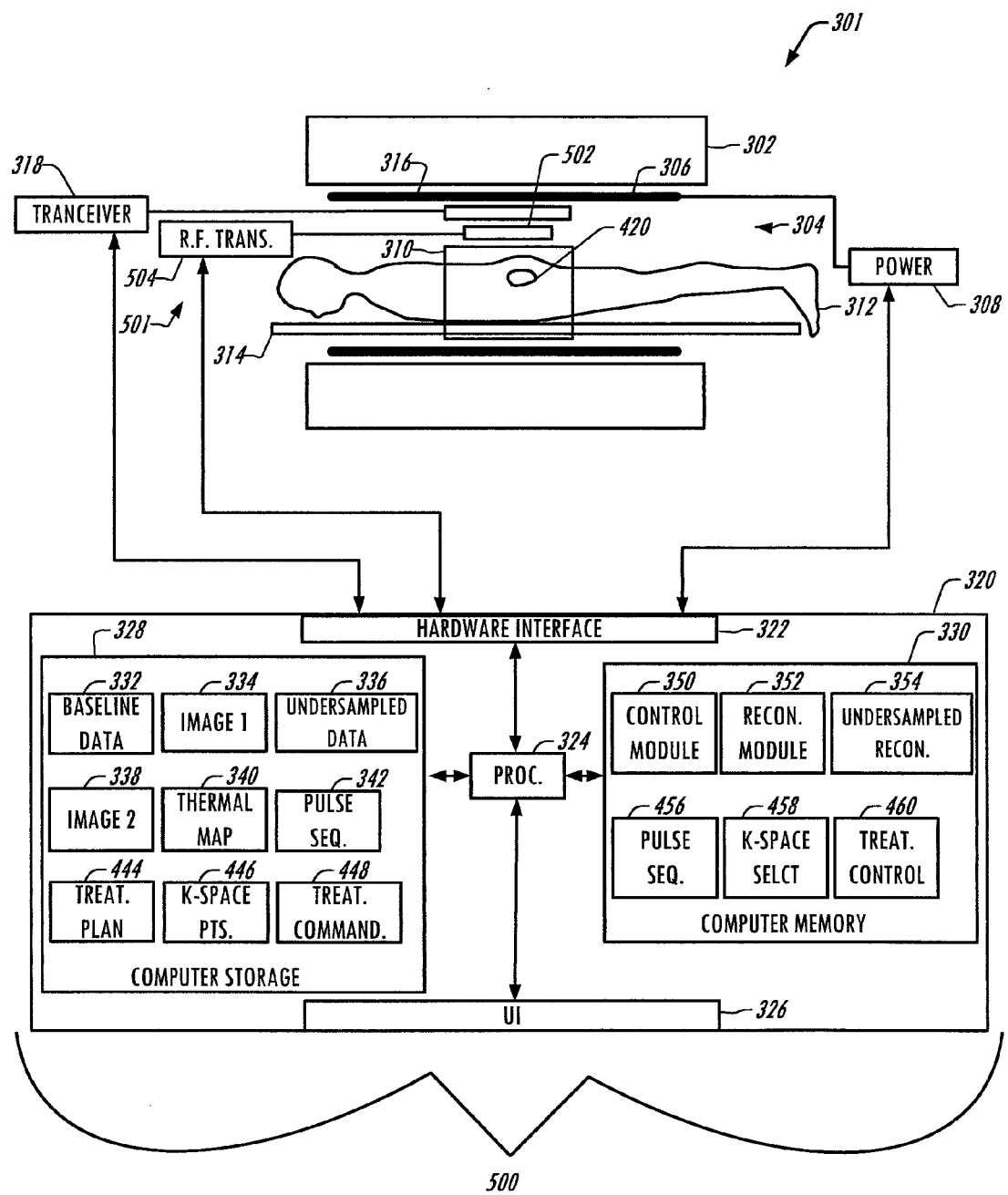
FIG. 5 illustrates a medical apparatus according to a further embodiment of the invention.

FIG. 5 shows a medical apparatus 500 according to a further embodiment of the invention. The embodiment shown in FIG. 5 is similar to that shown in FIGS. 3 and 4. The computer system 320 of FIG. 5 is equivalent to the computer system 320 shown in FIGS. 3 and 4 also. The contents of the computer storage 328 and the computer memory 330 are also equivalent to the computer storage 328 and the computer memory 330 as shown in FIGS. 3 and 4. In the embodiment shown in FIG. 5 a radio-frequency tissue heating system 501 is used as the temperature treatment system. The radio-frequency temperature treatment system 501 comprises an antenna 502 and a radio-frequency transmitter 504. The antenna 502 is in the vicinity of target zone 420. Radio-frequency energy generated by the transmitter 504 and radiated by the antenna 502 is used to selectively heat the target zone 420. In this embodiment the radio-frequency transmitter 504 is shown as being connected to the hardware interface 322. The processor 324 and the contents of the computer storage 328 and the computer memory 330 are used to control the radio-frequency transmitter 504 in a manner equivalent to the way the high-intensity focused ultrasound system 402 of FIG. 4 is controlled by the processor 324.

Figure 6:
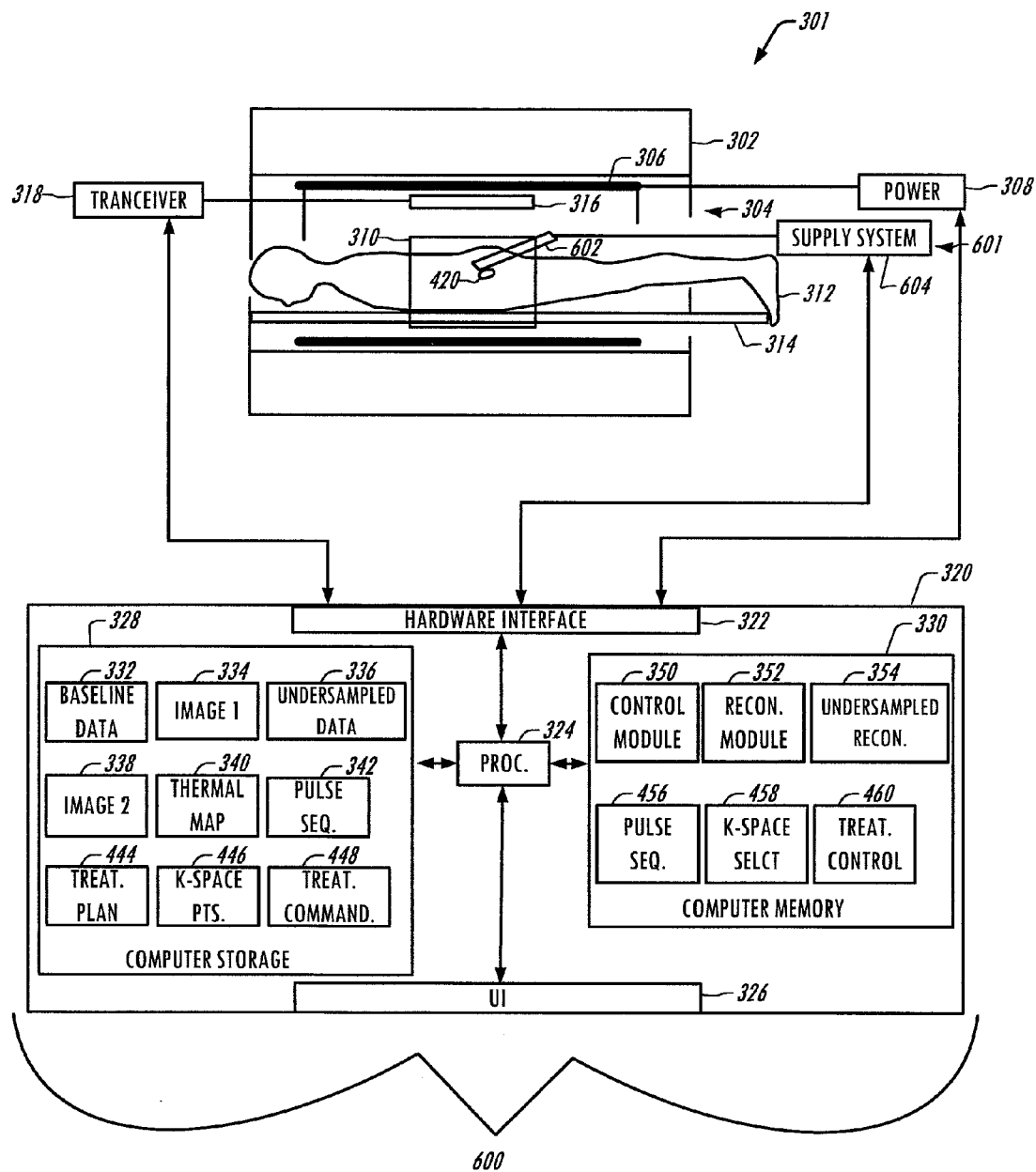
FIG. 6 illustrates a medical apparatus according to a further embodiment of the invention.

FIG. 6 shows a medical apparatus 600 according to a further embodiment of the invention. In this embodiment a thermal treatment system 601 is shown. There is an applicator 602 which has been inserted into the subject 312. Near the tip of the applicator 602 is the treatment zone 420. The thermal treatment system 602 here is representative and may be either a microwave applicator, a cryo-ablator, or a laser. The applicator 602 may be adapted for supplying microwave energy for delivering a cryogenic substance to the subject 312 or may be adapted for focusing laser light into the target zone 420. Likewise the supply system 604 may be a microwave power supply, a supply system with a cryogenic or cooling fluid, or it may be a laser power supply. The thermal treatment system 601 is shown as being connected to the hardware interface 322 of the computer system 330. The contents of the computer storage 328 and the computer memory 330 are equivalent to the embodiments shown in FIGS. 3, 4 and 5. The instructions and computer code contained therein allow the processor 324 to control the thermal treatment system 601 in a manner equivalent to the embodiments shown in FIGS. 4 and 5.

Figure 7:
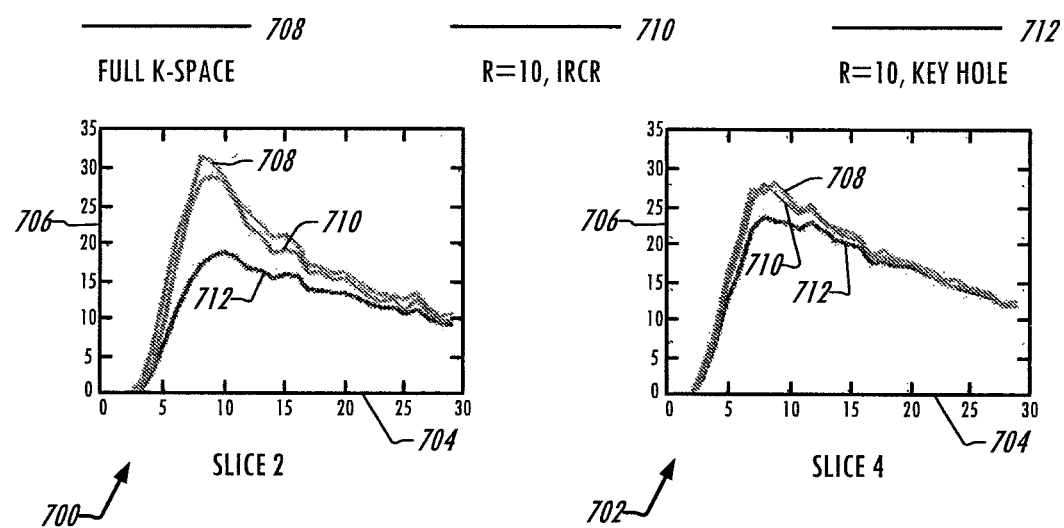
FIG. 7 shows two plots which illustrate the effectiveness of a method according to the invention.

FIG. 7 shows two plots 700, 702 which illustrate the effectiveness of the method. In the experiments shown in FIG. 7 a high-intensity focused ultrasound system was used to heat a target zone or region of interest of a pig. The temperature of the target zone or region of interest was imaged in a series of slices of magnetic resonance imaging data. Plot 700 shows data from slice 2 and plot 702 shows data from slice 4. The x-axis of both plots 700, 702, is the time in seconds 704. On the y-axis the temperature 706 in degrees Celsius above normal body temperature is shown. The temperature 706 in both plots 700, 702 is an average over the entire region of interest within that slice. Data was acquired using three different methods. Data acquired using the full k-space is labeled 708 in both plots. Data labeled 710 which used a reconstruction algorithm based on an IRCR method is labeled 710 in both plots. Data acquired using a keyhole algorithm for reconstructing the second image is labeled 712 in both images. Examining both slice 2 700 and slice 4 702, we see that the IRCR method 710 performs extremely well in comparison to acquiring the full k-space data 708.

In the example shown in FIG. 7, the temperature at the heated region or target zone was used to compare an IRCR method and key hole method. Only single channel data were available in this example. Full k-space data acquired at t=0, and 1 were used as baseline data. The net acceleration factor was 10.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A medical apparatus comprising:
   a magnetic resonance imaging system for acquiring magnetic resonance data;
   a processor for controlling the medical apparatus; and
   a memory containing machine readable instructions for execution by the processor, wherein execution of the instructions causes the processor to:
   acquire a first set of magnetic resonance data;
   reconstruct a first image using the first set of magnetic resonance data;
   acquire an undersampled magnetic resonance data set, wherein the undersampled magnetic resonance data set is undersampled in k-space in comparison to the first set of magnetic resonance data;
   reconstruct a second image using the undersampled magnetic resonance data set and the first image, wherein the second image is reconstructed using an image ratio constrained reconstruction algorithm; and
   calculate a temperature map using the second image.

2. The medical apparatus of claim 1, wherein the medical apparatus further comprises:
   a temperature treatment system for treating a target volume of a subject based on the temperature map.

3. The medical apparatus of claim 2, wherein execution of the instructions further causes the processor to select k-space sample points for the acquisition of the undersampled magnetic resonance data set in the target volume.

4. The medical apparatus of claim 2, wherein execution of the instructions further causes the processor to repeatedly:
   acquire the undersampled magnetic resonance data set;
   reconstruct the second image using the undersampled magnetic resonance data set and the first image;
   calculate the temperature map using the second image;
   generate temperature treatment system commands in accordance with the temperature map;
   send the temperature treatment system commands to the temperature treatment system.

5. The medical apparatus of claim 2, wherein the temperature treatment system includes one of: a high intensity focused ultrasound system, a radio-frequency tissue treating system, microwave applicator, a cryo-ablator, and a laser.

6. The medical apparatus of claim 2, wherein the reconstruction of the second image includes using the target volume as a constraint.

7. The medical apparatus of claim 1, wherein the first image is a phase image, and wherein the second image is a phase image, wherein calculating the temperature map includes determining a phase shift between voxels of the first image and voxels the second image.

8. The medical apparatus of claim 1, wherein calculating the temperature map includes calculating a change in any one of the following: proton density, T1 relaxation time of water protons, T2 relaxation time of water protons, T2-star relaxation time of water protons, and a diffusion constant.

9. The medical apparatus of claim 1, wherein reconstructing the second image includes constraining any one of the following: a magnitude image, a phase image, a complex image, and combinations thereof.

10. The medical apparatus of claim 1, further including:
    at least one of acquiring and/or reconstructing the first set of magnetic resonance data and the undersampled magnetic resonance data set with a parallel imaging technique.

11. The medical apparatus of claim 1, further including:
acquiring the first set of magnetic resonance data and the undersampled magnetic resonance data set includes controlling the magnetic resonance imaging system to apply a two-dimensional or a three-dimensional gradient echo pulse sequence.

12. The medical apparatus of claim 1, wherein acquiring the first set of magnetic resonance data and the undersampled magnetic resonance data set includes controlling the magnetic resonance imaging system to apply a two-dimensional or a three-dimensional echo planar imaging (EPI) pulse sequence, in which k-space sample points for the acquisition of the undersampled magnetic resonance data set and the first set of magnetic resonance data are chosen such that the first image and the second image are acquired using similar echo times.

13. The medical apparatus of claim 1, wherein acquiring the first set of magnetic resonance data and the undersampled magnetic resonance data set includes controlling the magnetic resonance imaging system to apply a two-dimensional or a three-dimensional spin echo or turbo spin echo pulse sequence.

14. A method of operating a medical apparatus wherein the medical apparatus comprises a magnetic resonance imaging system for acquiring magnetic resonance data; wherein the method comprises the steps of:
acquiring first magnetic resonance data;
reconstructing a first image using the first magnetic resonance data;
acquiring undersampled magnetic resonance data, wherein the undersampled magnetic resonance data is undersampled in k-space in comparison to the first magnetic resonance data;
reconstructing a second image using the undersampled magnetic resonance data and the first image, wherein the second image is reconstructed using an image ratio constrained reconstruction algorithm; and
calculating a temperature map using the second image.

15. The method of claim 14, wherein the first and second images include a target volume in the subject and wherein the temperature map is indicative of temperature in the target volume, the method further including:
controlling a therapy device to delivery therapy to the target volume in accordance with the temperature in the target volume indicated by the temperature map.

16. A non-transitory computer-readable medium carrying machine executable instructions for execution by a processor of a medical apparatus; wherein the medical apparatus comprises a magnetic resonance imaging system for acquiring magnetic resonance data; wherein execution of the instructions causes the processor to:
acquire a first magnetic resonance data set;
reconstruct a first image using the first magnetic resonance data set;
acquire an undersampled magnetic resonance data set, wherein the undersampled magnetic resonance data set is undersampled in k-space in comparison to the first magnetic resonance data set;
reconstruct a second image using the undersampled magnetic resonance data set and the first image, wherein the second image is reconstructed using an image ratio constrained reconstruction algorithm; and
calculate a temperature map using the second image.

17. A medical apparatus comprising:
a magnetic resonance imaging system configured to acquire magnetic resonance data from a region of a subject including a target volume;
a treatment device configured to deliver treatment to the target volume;
one or more processors configured to:
acquire a first set of magnetic resonance data from the magnetic resonance imaging system at a first time,
reconstruct the first set of magnetic resonance data into a first image including the target volume,
at a second time subsequent to the first time, acquire a second set of magnetic resonance data from the magnetic resonance imaging system, the second set of magnetic resonance data being undersampled in k-space relative to the first set of magnetic resonance data,
reconstruct the second set of magnetic resonance data into a second image including the target volume using the first image and an image ratio constrained reconstruction algorithm,
using the second image, calculate a temperature map indicative of temperature change in the target volume, and
control delivery of treatment to the target volume by the treatment device in accordance with the temperature map.

18. The medical apparatus of claim 17, wherein the one or more processors are further configured to repeatedly:
acquire subsequent undersampled magnetic resonance data sets,
reconstruct the subsequent undersampled magnetic resonance data sets into subsequent images using the first image,
update the temperature map using the subsequent images, and
update treatment system control commands in accordance with the updated temperature map.

* * * * *